(12) United States Patent
Hemker

(10) Patent No.: US 10,264,831 B1
(45) Date of Patent: Apr. 23, 2019

(54) POST OPERATIVE APPAREL

(71) Applicant: Lauren Hemker, Louisville, KY (US)

(72) Inventor: Lauren Hemker, Louisville, KY (US)

(*) Notice: Subject to any disclaimer, the term of this patent is extended or adjusted under 35 U.S.C. 154(b) by 69 days.

(21) Appl. No.: 15/200,720

(22) Filed: Jul. 1, 2016

(51) Int. Cl.
*A41D 13/00* (2006.01)
*A41D 13/12* (2006.01)
*A61F 5/03* (2006.01)
*A61F 7/02* (2006.01)
*A41B 1/08* (2006.01)
*A41D 1/22* (2018.01)
*A41D 27/20* (2006.01)

(52) U.S. Cl.
CPC .......... *A41D 13/1245* (2013.01); *A41B 1/08* (2013.01); *A41D 1/22* (2013.01); *A41D 27/20* (2013.01); *A61F 5/03* (2013.01); *A61F 7/02* (2013.01); *A41D 2600/00* (2013.01)

(58) Field of Classification Search
CPC . A41D 1/08; A41D 1/22; A41D 27/20; A41D 13/1245; A41B 1/08
USPC .............................................. 2/69, 463, 251
See application file for complete search history.

(56) References Cited

U.S. PATENT DOCUMENTS

| | | | | |
|---|---|---|---|---|
| 3,950,789 A * | 4/1976 | Konz | ................. | A41D 13/0055 2/93 |
| 4,666,432 A * | 5/1987 | McNeish | .............. | A61M 25/02 128/DIG. 26 |
| 5,524,293 A * | 6/1996 | Kung | ................. | A41D 13/0053 2/102 |
| 5,708,978 A | 1/1998 | Johnsrud | | |
| 6,055,668 A | 5/2000 | Gros et al. | | |
| 6,175,958 B1 * | 1/2001 | Wu | ........................... | F41H 1/02 2/102 |
| 6,477,710 B1 * | 11/2002 | Ojoyeyi | ............. | A41D 13/1236 2/114 |
| 6,692,413 B1 * | 2/2004 | Greenberg | ......... | A41D 13/0012 2/108 |
| 7,396,272 B1 * | 7/2008 | Newlen | ................ | A41C 3/0064 2/114 |
| 2004/0226073 A1 * | 11/2004 | McCullar | ........... | A41D 13/1245 2/114 |
| 2006/0253954 A1 * | 11/2006 | Music | ................ | A41D 13/0051 2/115 |
| 2008/0282441 A1 | 11/2008 | Green | | |
| 2010/0235963 A1 * | 9/2010 | Haydon | ............. | A41D 13/1245 2/207 |
| 2012/0260393 A1 * | 10/2012 | Crites | ...................... | A41B 1/00 2/67 |

(Continued)

Primary Examiner — Timothy K Trieu
(74) Attorney, Agent, or Firm — Middleton Reutlinger

(57) ABSTRACT

Post-operative apparel such as post-mastectomy garments are described herein. In various embodiments, a post-mastectomy garment may include first and second ends, an interior side and an exterior side opposite the interior side, and the interior and exterior sides may extend between the first and second ends. In some embodiments, a closing mechanism may releasably connect the first end to said second end. In various embodiments, two opposing openings through the garment may be provided and shaped to receive arms of a patient. In some embodiments, an adjustable chest support may extend outward from the interior side. One or more drain bulb pockets may be positioned on the interior side to receive one or more surgical drain bulbs. One or more tubing pockets may also be positioned on said interior side to receive excess drain tubing.

8 Claims, 4 Drawing Sheets

(56) References Cited

U.S. PATENT DOCUMENTS

| | | | |
|---|---|---|---|
| 2012/0291179 A1* | 11/2012 | Shea | A41D 27/20 |
| | | | 2/102 |
| 2014/0196189 A1 | 7/2014 | Lee et al. | |
| 2015/0026862 A1* | 1/2015 | Silverberg | A41D 13/0058 |
| | | | 2/69 |
| 2015/0320623 A1 | 11/2015 | Lee et al. | |
| 2015/0366276 A1 | 12/2015 | Kuzmanovski | |

* cited by examiner

POST OPERATIVE APPAREL

BACKGROUND

Various surgical procedures (e.g. mastectomies, lumpectomies, heart/chest surgeries, abdominal surgeries, etc.) require the placement of drainage tubes for draining fluids that accumulate in the wound bed following the procedure. If these fluids are allowed to accumulate they will put pressure on the surgical site that may cause a delay in healing, an increase in pain, and/or increase potential for bacterial infection. Thus, surgical drains are an important part of recovery from a surgical procedure. These drains may remain in place from one day to several weeks depending on the type of procedure and medical needs.

Bulbs attached to drainage tubing accumulate fluids and must be emptied periodically, usually every few hours. Patients recovering from surgical procedures often require a caretaker to assist them with daily tasks due to limited range of motion and strength. Existing post-operative garments are primarily focused on medical function and do not take into consideration the comfort and privacy of the patient. Therefore, it may be desirable to provide an easy to use post-operative garment that allows for proper storage of drain tubes and bulbs, while also allowing easy access for the caregiver and maintaining the privacy of the patient. Additionally or alternatively, it may be desirable to provide a post-operative garment with a chest support configured to provide comfort to the patient.

SUMMARY

Post-operative apparel such as post-mastectomy garments are described herein. In various embodiments, a post-mastectomy garment may include first and second ends, an interior side and an exterior side opposite the interior side, and the interior and exterior sides may extend between the first and second ends. In some embodiments, a closing mechanism may releasably connect the first end to said second end. In various embodiments, two opposing openings through the garment may be provided and shaped to receive arms of a patient. In some embodiments, an adjustable chest support may extend outward from the interior side. One or more drain bulb pockets may be positioned on the interior side to receive one or more surgical drain bulbs. One or more tubing pockets may also be positioned on said interior side to receive excess drain tubing.

In various embodiments, said closing mechanism may include a visual guide to aid in proper closure. In various embodiments, said chest support may be removably attached to the interior side. In various embodiments, the chest support further may include an adjustable closure that is adjustable between a plurality of positions to apply varying levels of tightness around a patient's chest.

In various embodiments, the chest support may be constructed with multiple layers defining a cavity therebetween, the chest support including a closed bottom and an open top that provides access to the cavity. In various embodiments, the chest support may be constructed with multiple layers and may include a closed bottom and a plurality of pockets accessible from a top of the chest support. In various embodiments, one or more drain bulb pockets may be comprised of a waterproof material.

In various embodiments, a port access site may be concealed by a pocket covering an opening connecting said interior side and said exterior side. In various embodiments, the port access site may be a closable opening above one of said opposing openings for receiving arms. In various embodiments, the closable opening may be secured by a hook and loop closure. In various embodiments, the garment may include two breast form pockets positioned on said interior side.

BRIEF DESCRIPTION OF THE DRAWINGS

In order that the embodiments may be better understood, embodiments of the post-operative garment will now be described by way of examples. These embodiments are not to limit the scope of the claims as other embodiments of the post-operative garment will become apparent to one having ordinary skill in the art upon reading the present description. Non-limiting examples of the present embodiments are shown in figures wherein:

DETAILED DESCRIPTION

Figure 1:
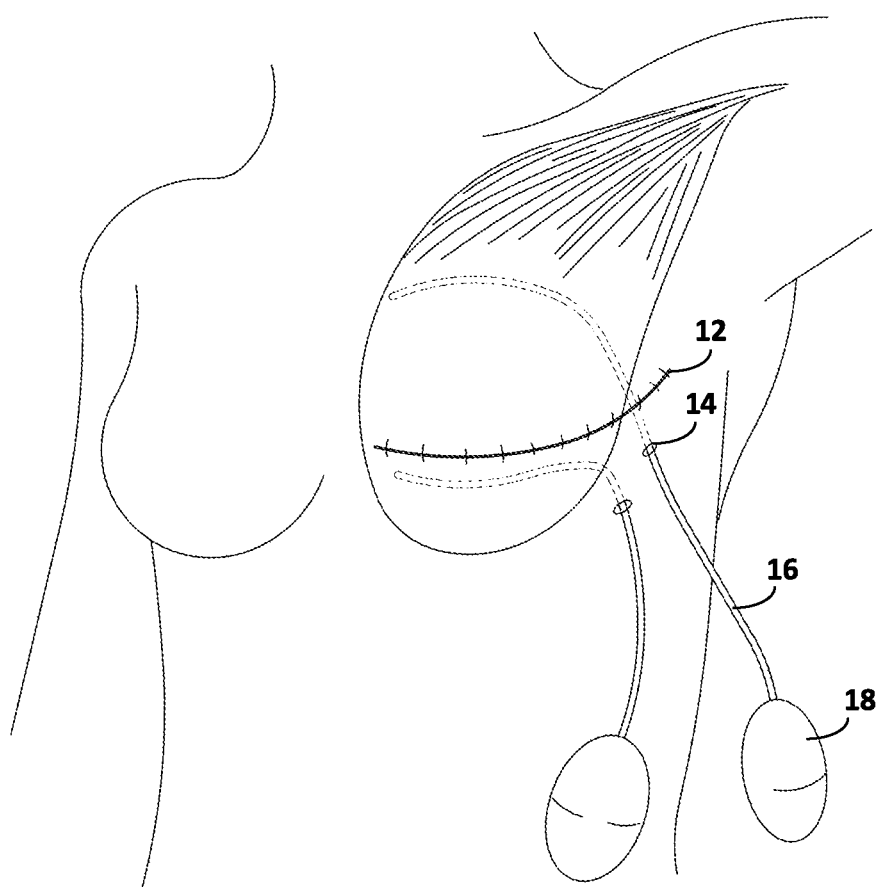
FIG. 1 depicts an example of drain placement following a mastectomy.

It is to be understood that the embodiments of post-operative garments and apparatus described herein are not limited in their application to the details of construction and the arrangement of components set forth in the following description or illustrated in the drawings. Other embodiments are capable of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings.

FIG. 1 depicts a front view of a patient following a mastectomy, and is an illustrative example of post-surgical drain placement. A surgical incision 12 may be made for various surgical procedures, for example a mastectomy. Subdermal drainage tubes 16 may be appropriately placed by the surgeon and, in many cases, additional drain incision(s) 14 may be made for the collection of fluids by drainage tubes 16. Tubing 16 may flow from the surgical site, through the drain incision 14, into a drain bulb 18 allowing blood and other fluids to properly drain from the wound bed. These drains 16 and bulbs 18 remain in place until the surgeon determines the appropriate time for removal, which may be a matter of days or weeks. In some cases, patients will be discharged from the hospital with surgical drains still in place. FIG. 1 is merely illustrative; drain number and placement may vary depending on a type or severity of the procedure, or even by the surgeon performing the surgery.

Figure 2:
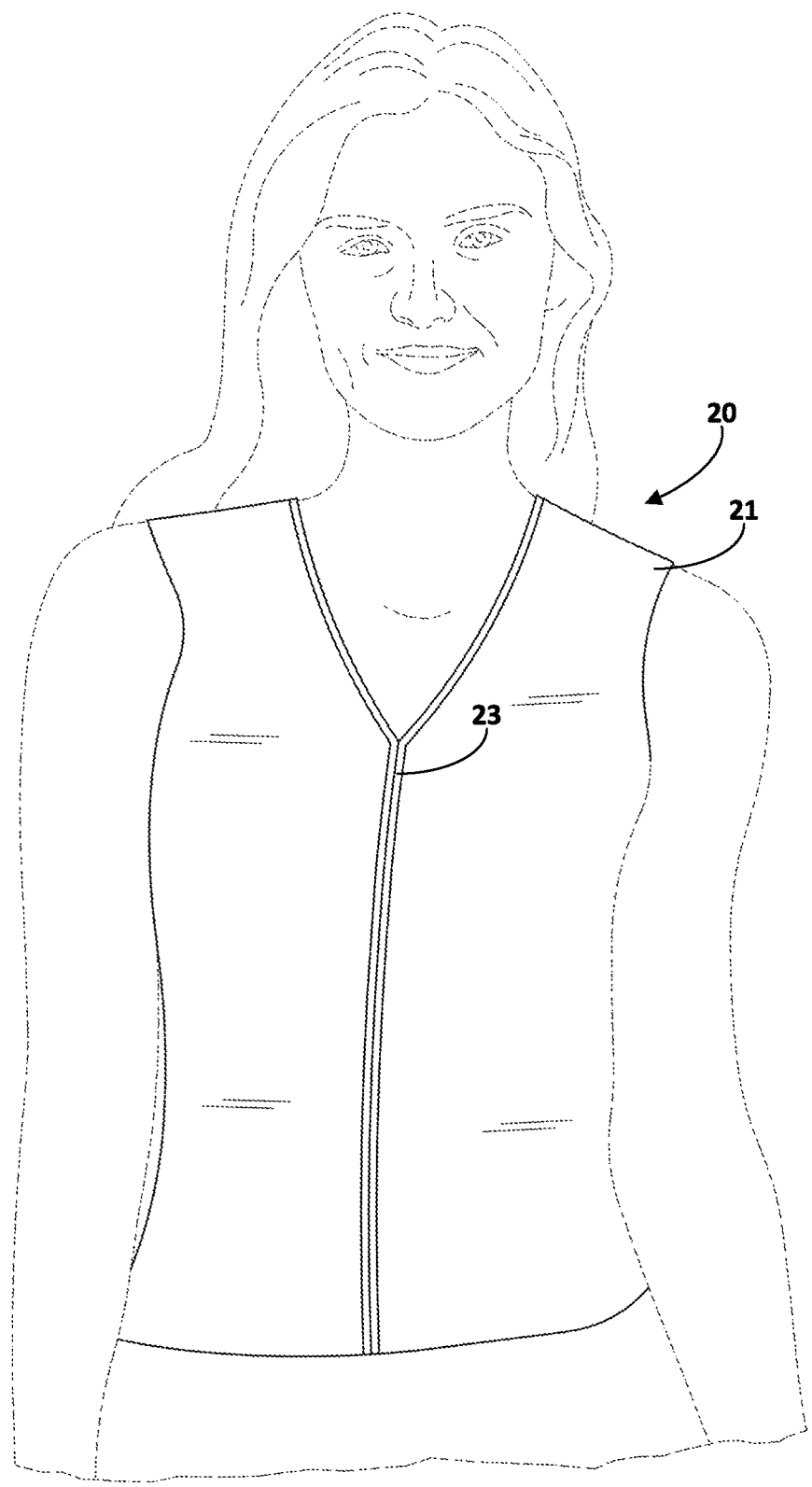
FIG. 2 is a front view of one embodiment of the closed post-operative garment worn by a user.
Figure 3:
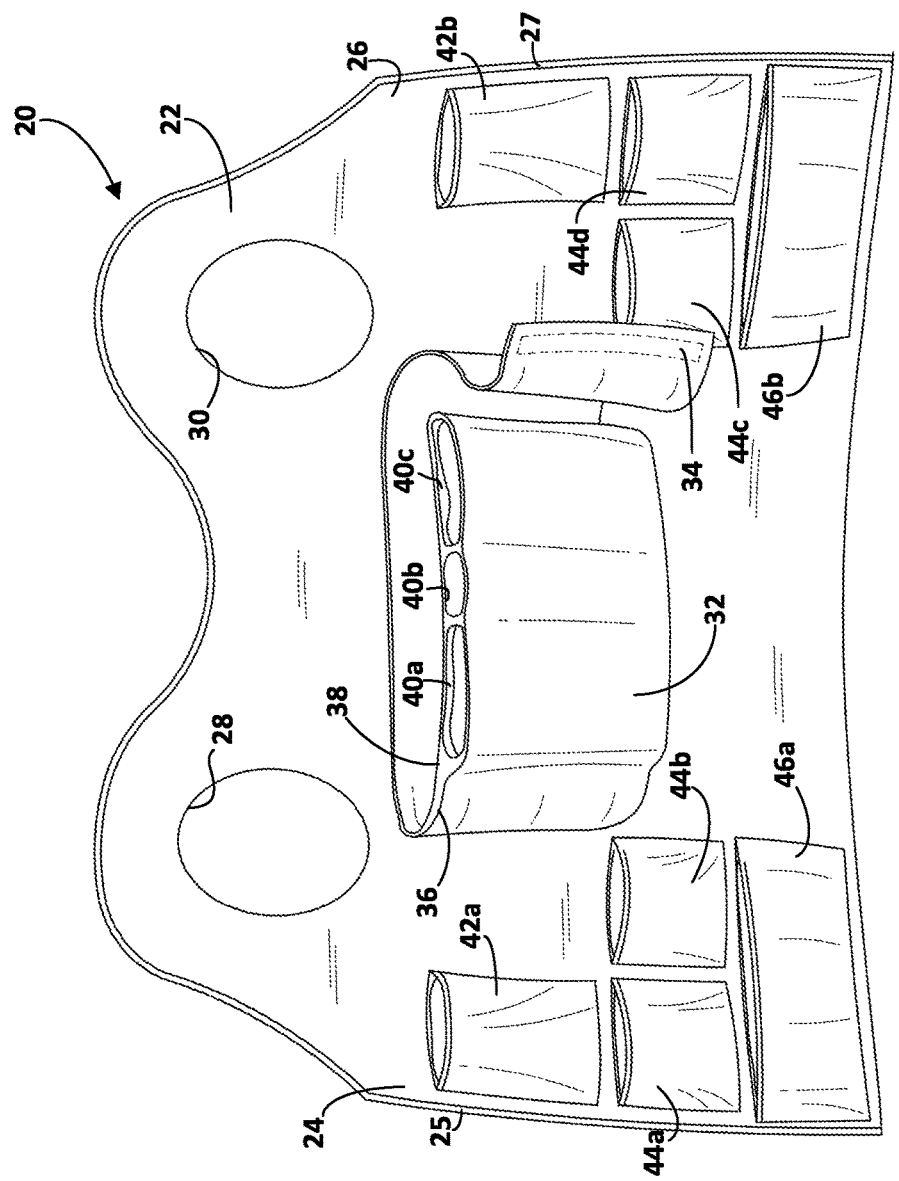
FIG. 3 is a front view of the post-operative garment of FIG. 2 fully opened exposing the interior of the garment.
Figure 4:
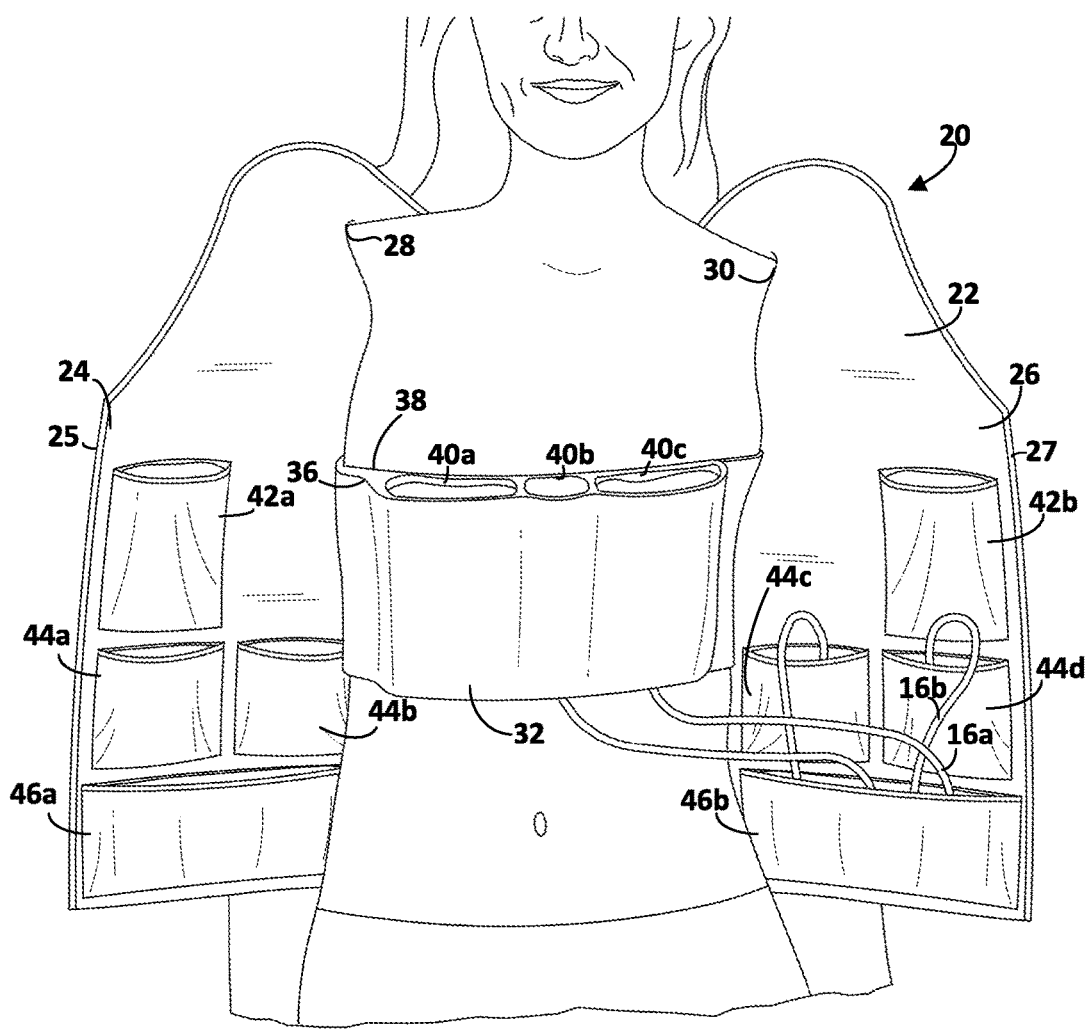
FIG. 4 is a front view of the post-operative surgical garment of FIG. 2 in an open configuration as it may be worn by a patient.

Referring now in detail to FIGS. 2-4, wherein like numerals indicate like elements throughout several views, there are shown in FIGS. 2 through 4 various views of an embodiment of a post-operative garment 20. Such a garment 20 may be used to provide a place to store drainage bulbs and tubes, as well as a chest support for patient comfort and privacy during the healing process.

Referring to FIG. 2, a front view of one embodiment of the post-operative garment 20 worn by a user is depicted in a closed configuration. The post-operative garment has an exterior side 21 and a front closure 23, which in this example comprises closures 25, 27 (see FIG. 3) coming together. These closures 25, 27 may be any type of closure allowing for opening and closing, such as hook and loop fasteners, buttons, snaps, zippers, etc. These closures 25, 27 may include a guide (not visible in FIG. 2) to assist the user or caregiver in ensuring the garment 20 is properly closed. Many surgical patients are simultaneously undergoing chemotherapy treatment, and thus may also have a port (not depicted), a small disc approximately the size of a quarter, positioned just under the skin and connecting to a large vein for delivery of chemotherapy drugs. The embodiment of FIG. 2 contains a wide and deep "V" shaped neckline allowing for access to the port site without having to undress. Other necklines are contemplated as well for enabling port site access, including but not limited to scoop necks, "Y" shaped necklines, sweetheart-shaped necklines, asymmetric necklines, Queen Anne necklines, off-shoulder necklines, boat necklines, etc.

Alternatively, some embodiments of the post-operative garment 20 may include a slit opening in the fabric, which may or may not be covered with an additional piece of fabric, to allow access to the port site without undressing or removing the garment 20. In other embodiments the post-operative garment 20 may further include a closure (not depicted) at or near the top of the shoulder(s) in order to allow access to the port without undressing or removing the garment. This closure may be any closure allowing for repeated opening and closing, for example hook and loop closure, buttons, snaps, zippers, etc.

Referring to FIGS. 3 and 4, front views of the post-operative garment 20 fully opened exposing an interior side 22 of the garment are depicted. The garment 20 may include opposing arm holes 28, 30 connecting the exterior side 21 (see FIG. 2) to the interior side 22. In some embodiments, the arm holes 28, 30 may have an additional closable opening (not depicted) at the top allowing for port access and/or adjustability of the garment size. The garment 20 may be closed (as depicted in FIG. 2) when a first end 24 of the garment 20 and a second end 26 of the garment 20 are brought together and closed. This closure between the first end 24 and the second end 26 may be accomplished by closures 25, 27, which as mentioned above may take the form of hook and loop closures, buttons, snaps, zippers, etc. The first end 24 and second end 26 may further contain visual indicia (not depicted in FIG. 3) that serves as a guide to ensure proper alignment and closure. This guide may allow the patient or caregiver to easily align and close the garment in a single attempt. The visual indicia may take the form of a color-coding system, a system of matching numbers, shapes, and/or letters between the two sides of the closure, etc.

The interior side 22 of the garment 20 may further include two breast form pockets 42a, 42b on opposing ends that may be sized to receive breast forms, if desired by the patient. The interior of the garment also may include one or more drain bulb pockets 44a, 44b, 44c, and 44d, for example two on each side of the garment 20, for storage of drain bulbs (not depicted in FIG. 3; see FIG. 1). In various embodiments, these drain bulb pockets 44a-d may be made of waterproof material to prevent fluid in the drain from coming into contact with the patient if the bulb is not correctly aligned or suctioned after being emptied. Use of a pocket made of a waterproof material also contains any spillage from the drain bulbs in one area, making cleanup easier.

In various embodiments, the interior side 22 of the garment 20 may further include one or more tubing pockets 46a, 46b for containing excess drain tubing (16 in FIGS. 1, 16a and 16b in FIG. 4). The length of tubing extending outward from the drain incision is typically selected to allow for the patient or caregiver to easily empty/replace drain bulbs. Consequently, there is often excess tubing that may hang out underneath a patient's clothing. There is a risk that this excess tubing might get caught on various household items (e.g. door handles, drawer pulls, etc.). One or more tubing pockets 46a, 46b for containing excess drain tubing 16 may confine and control the excess drain tubing 16 without preventing the flow of fluid into the drain bulbs. In some embodiments, tubing pockets 46a, 46b may also be waterproof and/or contain slip-resistant elements such as rubber pads, rubber seams, etc.

Extending outward from the interior side 22 of the garment 20 is a chest support 32. In some embodiments, the chest support 32 may be permanently attached to the interior side 22 of the garment 20, while in other embodiments the chest support 32 may be removably attached, for example through hook and loop, zipper, "belt loops," buttons, or snaps. In embodiments that include one or more belt loops, chest support 32 may be slid through one or more loops positioned on interior side 22 of garment 20. A removably attached chest support 32 allows the patient to decide if they desire the chest support at all. The chest support 32 may further provide patients with a sense of privacy and support. In some embodiments, the chest support 32 may include an adjustable closure 34 that is adjustable between a plurality of positions of varying tightness, allowing the chest support 32 to be wrapped around the patient's chest at a desired tightness. This adjustable closure 34 may be any closure known in the art, including, for example, hook and loop, buttons, zippers, belts, or snaps. In some embodiments, the component indicated at 34 may be a hook and loop fastener, and up to the entire front portion of chest support 32 may include complimentary hook and loop fasteners, allowing the patient maximum adjustability. This allows the patient the option of a tight, compression-like closure or a looser-fit closure depending on their personal preference or medical advice.

The chest support 32 of the garment 20 mimics bandaging techniques used in hospitals for post-surgical care. To this end, in some embodiments, chest support 32 may be constructed with various fabrics that may or may not be stretchable to various degrees. For those patients with surgical procedures affecting the chest and/or underarm area, traditional bras and tops—even those designed specifically for post-surgical use—may chafe against the surgical wound(s). The chest support 32 of the garment 20 as described herein allows the patient to comfortably enclose and support the wound areas to prevent such chafing.

In some embodiments, the chest support 32 may include a double-layer construction, including a first layer 36 and a second layer 38. When the garment 20 is worn by a patient, the first layer 36 and second layer 38 may be closed at the bottom of the chest support 32, while there may be one or more openings 40a, 40b, 40c into a space between the first layer 36 and the second layer 38 at the top of chest support 32. These openings 40a-c may provide access to an open cavity between the first layer 36 and the second layer 38 of the chest support 32 that is closed at the bottom between the two layers. Various therapeutic items such as ice packs or heat packs may be inserted into this cavity between the first layer 36 and the second layer 38, e.g., to apply hot or cold temperature to the patient's chest. In some embodiments, only the top portion of the chest support 32 that would wrap around the front of the patient, e.g., in front of her breasts, is open. In other embodiments, the entire top portion of the chest support 32 may be open. In some embodiments the double-layer construction includes a single opening or pocket for the insertion of therapeutic items. In other embodiments, such as that depicted in FIG. 3, the double-layer construction comprises a plurality of openings 40a, 40b, 40c for the insertion of therapeutic items.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification, unless clearly indicated to the contrary, should be understood to mean "at least one."

The phrase "and/or," as used herein in the specification, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of," or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A post-operative garment, comprising:
   first and second ends;
   an interior side and an exterior side opposite the interior side, wherein the interior and exterior sides extend between the first and second ends;
   a closing mechanism releasably connecting said first end to said second end;
   two opposing openings, shaped to receive the patient's arms, connecting said interior side and said exterior side;
   an adjustable chest support that includes a fastener for removably coupling with the interior side,
   wherein the chest support further comprises multiple layers defining a cavity therebetween, and the chest support includes a closed bottom and an open top that provides access to the cavity,
   wherein, when worn by the patient, the cavity is positioned adjacent to the patient's chest;

wherein said chest support further includes a plurality of pockets within the cavity accessible from the open top of the chest support;

two or more drain bulb pockets positioned adjacent each other on said interior side shaped to receive one or more surgical drain bulbs, wherein each of the two or more drain bulb pockets includes a closed bottom and a top opening; and one or more tubing pockets positioned on said interior side shaped to receive excess drain tubing, wherein each of the one or more tubing pockets includes a closed bottom and a top opening;

wherein the top opening of the two or more drain bulb pockets is positioned above the top opening of the one or more tubing pockets.

2. The post-operative garment of claim 1 wherein said closing mechanism further comprises a visual guide to aid in proper closure.

3. The post-operative garment of claim 1 wherein the chest support further comprises an adjustable closure that is adjustable between a plurality of positions to apply varying levels of tightness around a patient's chest.

4. The post-operative garment of claim 1 wherein said two or more drain bulb pockets are comprised of a waterproof material.

5. The post-operative garment of claim 1 wherein the garment further comprises two breast form pockets positioned on said interior side.

6. A post-operative garment, comprising:

an interior side and an exterior side extending between a first end and a second end of the garment;

a closing mechanism releasably connecting said first end to said second end, wherein said closing mechanism further comprises a guide to ensure proper closure;

two opposing openings shaped to receive arms of a wearer, wherein the opposing openings connect said interior side and said exterior side;

an adjustable chest support that includes a fastener for removably coupling with the interior side, wherein said adjustable chest support extends outward from said interior side, and said adjustable chest support comprises a double-layers construction with a cavity therebetween, a closed bottom and an open top that provides access to the cavity, wherein the cavity further comprises a plurality of openings on top to define a plurality of pockets, wherein said adjustable chest support is adjustable between a plurality of positions of varying tightness around the patient's chest when worn, and wherein, when worn by the patient, the cavity is positioned adjacent to the patient's chest;

two breast form pockets positioned on said interior side, wherein each breast form pocket is shaped to receive a breast form;

two or more drain bulb pockets positioned adjacent each other on said interior side sized to receive surgical drains, wherein each of the two or more drain bulb pockets includes a closed bottom and a top opening, and wherein said two or more drain bulb pockets are comprised of waterproof material; and one or more tubing pockets positioned on said interior side and shaped to receive excess drain tubing, wherein each of the one or more tubing pockets includes a closed bottom and a top opening, and wherein the top opening of the two or more drain bulb pockets is positioned above the top opening of the one or more tubing pockets.

7. The post-operative garment of claim 6 wherein the cavity is sized to receive an ice or heat pack.

8. The post-operative garment of claim 6, wherein the one or more tubing pockets are constructed with waterproof material.

* * * * *